US012232918B2

(12) United States Patent
Alemany

(10) Patent No.: US 12,232,918 B2
(45) Date of Patent: Feb. 25, 2025

(54) BACTERIA SPREAD PREVENTION TOOL FOR ORAL PROCEDURES

(71) Applicant: Juan C. Alemany, Boqueron, PR (US)

(72) Inventor: Juan C. Alemany, Boqueron, PR (US)

( * ) Notice: Subject to any disclaimer, the term of this patent is extended or adjusted under 35 U.S.C. 154(b) by 871 days.

(21) Appl. No.: 17/396,929

(22) Filed: Aug. 9, 2021

(65) Prior Publication Data

US 2022/0039933 A1 Feb. 10, 2022

Related U.S. Application Data

(60) Provisional application No. 63/063,908, filed on Aug. 10, 2020.

(51) Int. Cl.
*A61C 19/00* (2006.01)
*A47C 7/74* (2006.01)
*A61B 90/00* (2016.01)
*A61B 90/40* (2016.01)
*A61G 10/00* (2006.01)
*A61G 13/10* (2006.01)
*A61G 15/10* (2006.01)
A61C 17/00 (2006.01)
A61L 9/00 (2006.01)
F24F 3/163 (2021.01)

(52) U.S. Cl.
CPC ................ *A61C 19/00* (2013.01); *A47C 7/74* (2013.01); *A61B 90/05* (2016.02); *A61B 90/40* (2016.02); *A61G 10/005* (2013.01); *A61G 13/108* (2013.01); *A61G 15/10* (2013.01); A61C 17/00 (2013.01); A61L 9/00 (2013.01); F24F 3/163 (2021.01)

(58) Field of Classification Search
CPC ......... A61C 19/00; A61C 17/00; A61C 17/06; A47C 7/74; A61B 90/05; A61B 90/40; A61B 2090/401; A61G 10/005; A61G 13/108; A61G 15/10; A61L 9/00; F24F 3/163
See application file for complete search history.

(56) References Cited

U.S. PATENT DOCUMENTS

| 4,252,054 A | * | 2/1981 | Bakels | A61G 15/14 55/385.2 |
| 4,865,049 A | * | 9/1989 | Gatti | A61B 18/00 128/849 |
| 4,936,318 A | * | 6/1990 | Schoolman | A61G 13/108 15/301 |
| 4,981,324 A | * | 1/1991 | Law | A47C 7/74 5/423 |

(Continued)

*Primary Examiner* — Dung H Bui
(74) *Attorney, Agent, or Firm* — Brennan, Manna & Diamond, LLC

(57) ABSTRACT

This present invention relates to a bacteria spread prevention tool designed to be used during oral procedures and is used to prevent the smear or spread of bacteria and viruses. The bacteria spread prevention tool comprises a slightly curved polycarbonic device having an interior suction mechanism. The prevention tool can be placed 4 to 6 inches from the oral cavity of a user, thereby forming a barrier between the user's mouth and the dental care professional, in order to prevent the spread of bacteria, or other pathogens via the oral cavity during dental health checkups or dental procedures. The transparent polycarbonic device provides access to the oral cavity while blocking the spread of aerosols and pathogens.

16 Claims, 4 Drawing Sheets

(56) References Cited

U.S. PATENT DOCUMENTS

| | | | | |
|---|---|---|---|---|
| 6,071,419 | A * | 6/2000 | Beier | B01D 39/1623 |
| | | | | 210/488 |
| 10,663,183 | B1 * | 5/2020 | Stewart | F24F 8/158 |
| 10,821,202 | B1 * | 11/2020 | Chase | A61M 16/1065 |
| 2002/0137982 | A1 * | 9/2002 | Taylor | A61B 17/00 |
| | | | | 600/37 |
| 2005/0173950 | A1 * | 8/2005 | Bajic | A47C 7/74 |
| | | | | 297/452.45 |
| 2005/0252181 | A1 * | 11/2005 | Ranalli | B01D 45/08 |
| | | | | 55/446 |
| 2007/0042702 | A1 * | 2/2007 | Jeng | F24F 3/163 |
| | | | | 454/187 |
| 2009/0019822 | A1 * | 1/2009 | Feisthammel | F24C 15/2035 |
| | | | | 55/385.4 |
| 2014/0146519 | A1 * | 5/2014 | Chang | A61L 9/205 |
| | | | | 362/96 |
| 2016/0018117 | A1 * | 1/2016 | Sekiguchi | A61B 90/13 |
| | | | | 96/418 |
| 2019/0075985 | A1 * | 3/2019 | King | A47L 9/10 |

* cited by examiner

BACTERIA SPREAD PREVENTION TOOL FOR ORAL PROCEDURES

CROSS-REFERENCE TO RELATED APPLICATION

The present application claims priority to, and the benefit of, U.S. Provisional Application No. 63/063,908, which was filed on Aug. 10, 2020 and is incorporated herein by reference in its entirety.

FIELD OF THE INVENTION

The present invention relates generally to the field of dental appliances. More specifically, the present invention relates to tools used in oral care procedures that inhibit the spread of bacteria to oral care professionals, and act as a barrier between the user's or patient's mouth and the oral care professionals during any dental procedure. The bacteria prevention tool comprises a transparent curved polycarbonic shield having an interior suction mechanism for collecting viruses, bacteria, or other pathogens from a user's mouth, and for reducing droplet spatter during operative dental procedures. The invention is advantageous in reducing the risk of experiencing any infection spread during dental procedures. Accordingly, the present disclosure makes specific reference thereto. Nonetheless, it is to be appreciated that aspects of the present invention are also equally applicable to other like applications, devices and methods of manufacture.

BACKGROUND OF THE INVENTION

By way of background, various kinds of harmful pathogens, viruses, bacteria and more are present in the surroundings which causes the spread of various infectious diseases. Such harmful pathogens are not normally visible to humans, and can be incredibly dangerous if inhaled by the user, possibly leading to serious illnesses. Some of the infectious diseases are airborne and can be easily and quickly spread from one person to another if the harmful pathogens in the environment are inhaled. In the times of pandemics such as COVID-19, which is an epidemic of any disease that has spread across a large region, such as multiple continents or worldwide, affecting a substantial number of individuals, and caused by the exponential spread of a virus, bacteria or other pathogen causing the infectious disease. With or without an active epidemic, there is always a need for individuals to protect themselves from the transmission of harmful pathogens. Such infectious diseases, if not properly controlled, can take a toll on people's health, well-being and life.

People typically wear protective face masks and intensify efforts to maintain their personal hygiene to prevent the spread of infectious diseases, especially in the times of pandemics such as COVID-19. Usually, people wear face masks, face shields, and other accessories while going in places such as markets, schools, hospitals, offices, etc. The face masks or face shields act as a barrier between the oral and nasal passage of the user and the surrounding ambient air, therefore preventing the users from being infected due to the inhalation of harmful germs, bacteria, viruses or other pathogens present in the environment.

However, while visiting dental care centers for any dental procedure or oral health checkup, users are required to remove their protective face mask, so that the dentist or other oral care professional can visually check the oral health of the users. When the mask is removed, there is no barrier between the oral and nasal passages of the patient and the environment, causing a significant risk of patients or professionals becoming infected. Additionally, if the patient is already infected, there is a risk of the infection spreading to the dentist and other oral care professionals that are present in an examination room. Repeated examinations of individual patients that have tested positive for a virus places other patients and dental care professionals at risk for contracting same. It is to be appreciated that while performing dental treatment procedures on a patient, the dentist's face and the patient's mouth are in close proximity. Additionally, dental procedures are typically accompanied by a great deal of droplet splatter from the patient's mouth, directed at the dentist's face and eyes. This droplet splattering can result in viral transmission. In such cases, both the patients and the dentists may feel uncomfortable receiving and providing treatments if there is a high risk of infection.

Therefore, there exists a long felt need in the art for a device for dental health care centers which can be used to prevent the spread of harmful germs, bacteria, viruses, pathogens and the like. There is also a long felt need in the art for a bacteria prevention tool which can be conveniently used by the oral care professionals while checking the oral health of their patients, or while performing any dental treatment procedure. Additionally, there is a long felt need in the art for a barrier device which allows dental professionals to easily check the oral health of their patients while being protected against transmission of infectious diseases. Moreover, there is a long felt need in the art for a barrier device which prevents droplet splatter expelled from the patient's mouth from transmitting to an oral care professional in close proximity to the patient. Further, there is a long felt need in the art for a bacteria prevention tool which enables dentists to easily check their patients without worrying about being infected. Finally, there is a long felt need in the art for a bacteria prevention device which gives a sense of relief to the patients as well as to the oral care professionals, and provides reassurance and comfort during dental checkups or dental treatment procedures.

The subject matter disclosed and claimed herein, in one embodiment thereof, comprises an oral procedure bacteria prevention tool designed to stop the smear or spread of bacteria and viruses. The prevention tool comprises: an outer or top transparent polycarbonic layer; an inner or bottom transparent polycarbonic layer; the top transparent polycarbonic layer and the bottom transparent polycarbonic layer are joined together at a pair of longitudinal edges and a pair of lateral edges; the top transparent polycarbonic layer and the bottom transparent polycarbonic layer are bent or curved up to forty degrees, and can include a space therebetween of ten millimeters; the bottom layer having a pattern of small holes to deflect and collect smears, splatters, pathogens, and/or aerosols; the top layer further having a quick connector to attach to a high-volume suction mechanism; and, the oral procedure bacteria prevention tool having a stand placed on a floor including an arm removably attached to the oral procedure bacteria prevention tool to position same at a suitable location. An exemplary suitable position can be up to six inches from the oral cavity of a patient during an oral procedure.

In this manner, the novel bacteria spread prevention tool of the present invention accomplishes all of the forgoing objectives, and provides a relatively safe, easy, convenient and efficient solution for oral care professionals and dental patients, which can be used during dental checkups and dental treatment procedures to prevent the spread of any harmful pathogens, bacteria, viruses or more. The bacteria spread prevention tool of the present invention is also user friendly, as it gives a sense of relief to patients and dentists while the dental procedures are performed, and protects them from being infected by any diseases during such procedures.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises an oral procedure bacteria spread prevention tool designed to stop the smear or spread of bacteria and viruses. The prevention tool comprises: an outer or top transparent polycarbonic layer; an inner or bottom transparent polycarbonic layer; the top transparent polycarbonic layer and the bottom transparent polycarbonic layer are joined together at a pair of longitudinal edges and a pair of lateral edges; the top transparent polycarbonic layer and the bottom transparent polycarbonic layer are bent or curved up to forty degrees, and can include a space therebetween of ten millimeters; the bottom layer having a pattern of small holes to deflect and collect smears, splatters, pathogens, and/or aerosols; the top layer further having a quick connector to attach to a high-volume suction mechanism; and, the oral procedure bacteria spread prevention tool having a stand placed on a floor including an arm removably attached to the oral procedure bacteria spread prevention tool to position same at a suitable location. An exemplary suitable position can be up to six inches from the oral cavity of a patient during an oral procedure.

In a further embodiment of the present invention, a pathogen smear or spread protection apparatus to prevent the spread of pathogens via the oral and nasal cavities during an oral procedure is disclosed and comprises at least two layers of transparent polycarbonic layers. The layers can have a space of generally about ten millimeters therebetween, and can include a plurality of holes to collect pathogens. The spread protection apparatus further includes a quick connector to attach to a high-volume suction mechanism to provide suction of the oral cavity of a patient. The pathogen smear or spread protection apparatus provides a shield for the oral care practitioner while providing access to the oral cavity of a user or patient.

The oral procedure bacteria spread prevention tool of the present invention allows an oral care practitioner and other staff to be safe from pathogens and uses an internal suction mechanism to prevent the spread of pathogens via the oral cavity. The bottom layer has a pattern of small holes to collect the smears, splatters, pathogens and/or aerosols and acts as a physical barrier between the patient and health care professional. The polycarbonic layers are ergonomically designed to provide convenient access to the mouth of a patient.

The advantage of the oral procedure bacteria spread prevention tool of the present invention is that it may be placed at any convenient position, such as six inches from the oral cavity of a patient. The tool may be used for all types of oral procedures and may be useful for all positions of oral procedures. The spread prevention tool enables access to a patient's oral cavity while providing the protection to staff from pathogens.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
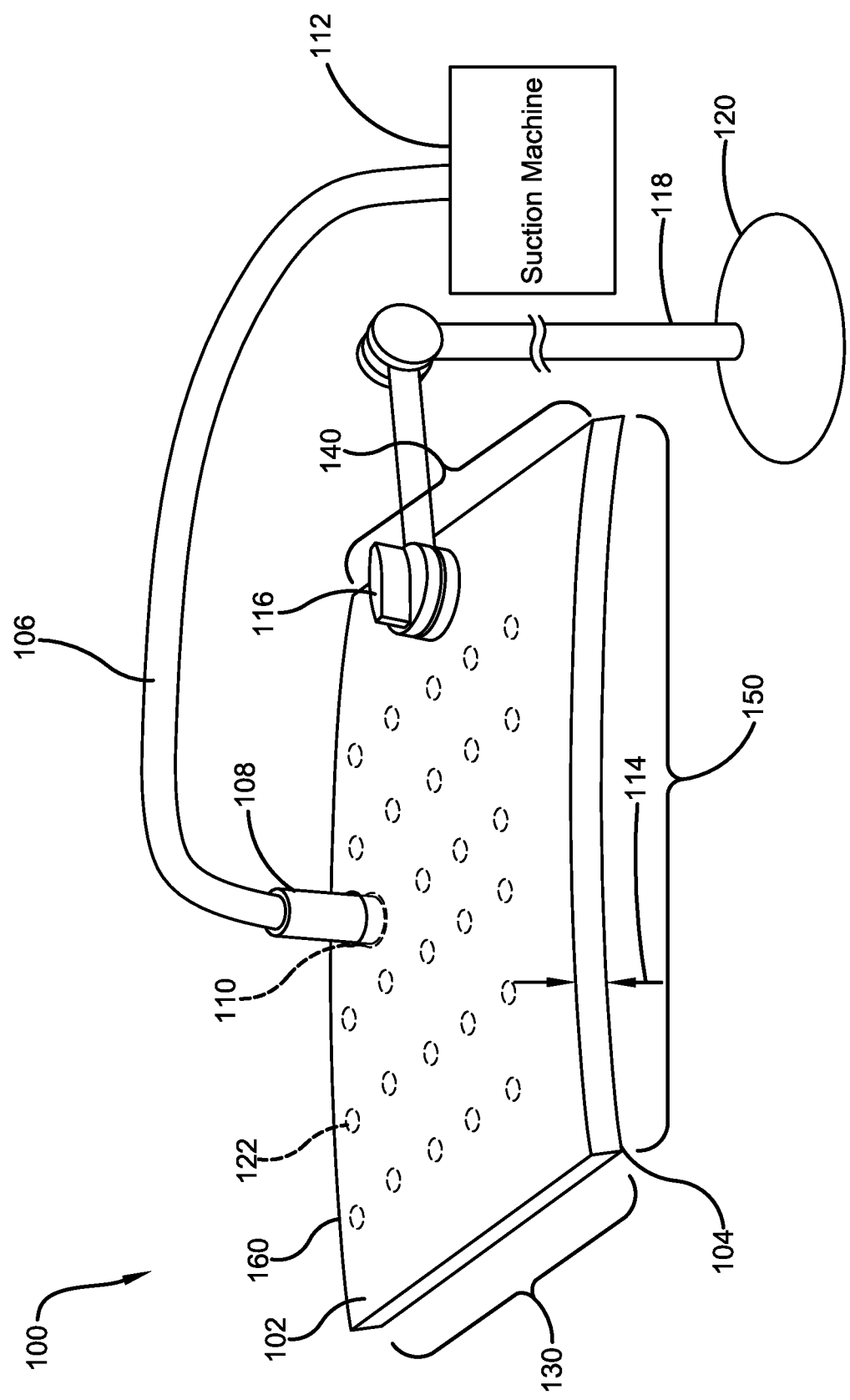
FIG. 1 illustrates a top perspective view of one potential embodiment of an oral procedure bacteria prevention tool of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention, and do not limit the scope of the invention. Additionally, an illustrated embodiment need not have all the aspects or advantages shown. Thus, in other embodiments, any of the features described herein from different embodiments may be combined.

As noted above, there exists a long felt need in the art for a device for dental health care centers which can be used to prevent the spread of harmful germs, bacteria, virus, pathogens and the like. There is also a long felt need in the art for a bacteria spread prevention tool which can be conveniently used by oral care professionals while checking the oral health of their patients or while performing dental treatment procedures. Additionally, there is a long felt need in the art for a barrier device which allows dentists to easily check the oral health of their patients while being protected against transmission of infectious diseases. Moreover, there is a long felt need in the art for a barrier device which prevents droplet splatters and aerosols from the patient's mouth from spreading and possible viral transmission from same. Further, there is a long felt need in the art for a bacteria spread prevention tool which enables dentists to easily check their patients without worrying about being infected. Finally, there is a long felt need in the art for a bacteria spread prevention device which gives a sense of relief to the patients as well as to the oral care professionals, and makes them comfortable during dental check-ups or dental treatment procedures.

The subject matter disclosed and claimed herein, in one embodiment thereof, comprises an oral procedure bacteria spread prevention tool designed to stop the smear or spread of bacteria and viruses. The prevention tool comprises: an outer or top transparent polycarbonic layer; an inner or bottom transparent polycarbonic layer; the top transparent polycarbonic layer and the bottom transparent polycarbonic layer are joined together at a pair of longitudinal edges and a pair of lateral edges; the top transparent polycarbonic layer and the bottom transparent polycarbonic layer are bent or curved up to forty degrees, and can include a space therebetween of ten millimeters; the bottom layer having a pattern of small holes to deflect and collect smears, splatters, pathogens and/or aerosols; the top layer further having a quick connector to attach to a high-volume suction mechanism; and, the oral procedure bacteria spread prevention tool having a stand placed on a floor including an arm removably attached to the oral procedure bacteria spread prevention tool to position same at a suitable location. An exemplary suitable position can be up to six inches from the oral cavity of a patient during an oral procedure.

Referring initially to the drawings, FIG. 1 illustrates a perspective view of an oral procedure bacteria spread prevention tool of the present invention in accordance with the disclosed structure. The oral procedure bacteria spread prevention tool 100 is a bacteria spread prevention tool designed to stop the spread of viruses and bacteria by blocking the spread of pathogens while providing access to the oral cavity of a patient by an oral care professional.

The oral procedure bacteria spread prevention tool 100 has two layers of transparent polycarbonic layers that can be slightly bent in the middle to form a convex shape for both of the two layers of transparent polycarbonic layers. The top layer 102 and the bottom layer 104 are of substantially the same size, and are connected at a pair of opposite longitudinal sides 130, 140 and a pair of opposite lateral sides 150, 160. A gap 114 of generally about 5 mm to about 15 mm, for example, is maintained between the top layer 102 and the bottom layer 104, such that the top layer 102 and the bottom layer 104 do not touch each other except around a perimeter at the longitudinal sides 130, 140 and the lateral sides 150, 160.

The bottom layer 104 has a pattern of small holes 122 for enabling the transmission of some aerosols, pathogens, viruses, etc. to pass therethrough, while at the same time deflecting droplets and splatters downward, away from the oral care professional. The top layer 102 does not include any holes or passages. Thus, the aerosols, etc. that pass through the holes 122 of the bottom layer 104 become trapped between the bottom layer 104 and the top layer 102. The top layer 102 includes a quick connector 108 via a hole 110 which is attached to a high-volume suction machine 112 with a suction pipe 106. When the suction machine 112 is turned on, a constant extraction airflow is maintained to the air space between the bottom layer 104 and the top layer 102. Any aerosols or other pathogens are removed from the work area, thereby inhibiting their transmission to the surrounding ambient air and to the other oral care professionals in proximity to the patient.

The oral procedure bacteria prevention tool 100 is transparent and ergonomically designed such that when placed 4 to 6 inches from the oral cavity of a user during an oral procedure, the oral cavity or the mouth of the user can still be easily accessed by the oral care professional. The oral procedure bacteria prevention tool 100 allows use of an external vacuum at a convenient distance from the work area without having to manually hold the suction tube 106 or the connector 108, thereby eliminating the potential of pathogen spread and viral transmission. The oral procedure bacteria spread prevention tool 100 acts as a physical barrier to minimize direct exposure to both aerosols and droplet spatters during an oral procedure. With the use of the tool 100, necessary aerosol-generating oral procedures may also be performed without compromising the safety of the staff and the patient.

To place the oral procedure bacteria prevention tool 100 at a convenient height and distance from the oral cavity of a patient, an adjustable stand 118 is arranged to connect to the tool 100 at one end, and to position at an appropriate place through a stand connector 116 at another end. The stand 118 has a base 120 that can selectively be mounted to the floor, wall or ceiling. The stand 118 may be detachable from the tool 100, and is lightweight and portable. The arm of the stand 118 is adjustable and may be positioned to meet different reaches and heights based on the position of a patient and the requirements of the oral care professionals.

The top layer 102 includes the connector hole 110 positioned close to the lateral edge 160 and in a central position. The connector hole 110 allows the high-volume suction pipe 106 to be attached to the tool 100 through the suction connector 108. The connector hole 110 can be 5 to 10 mm in diameter to securely accommodate the suction pipe 106 into the tool 100. In one potential embodiment, the quick connector 108, connected to the high suction machine 112, is 5-10 mm in diameter in order to provide an unobstructed view and a suction mechanism sized for effective air extraction from the space between the bottom layer 104 and the top layer 102. The tool 100 acts as a shield between the oral care professionals and the patients, while providing a convenient and safe environment for the oral procedure.

The material of the oral procedure bacteria spread prevention tool 100 is strong, tough, optically transparent, lightweight, cost-effective and impact-resistant. The top layer 102 and the bottom layer 104 can be joined together at the longitudinal edges and the lateral edges by an adhesive, such as an acrylic glue.

The polycarbonate layers are washable and may be sanitized after every use. The longitudinal edges and the lateral edges can comprise heavy plastic, metal or steel. The stand connector stabilizes the tool 100 while performing the oral procedure. In one embodiment, dimensions of the oral procedure bacteria spread prevention tool 100 is 12" (L)× 16" (W)×1" (H). Alternatively, dimensions of the oral procedure bacteria spread prevention tool 100 is 15" (L)×18" (W)×1.5" (H).

Figure 2:
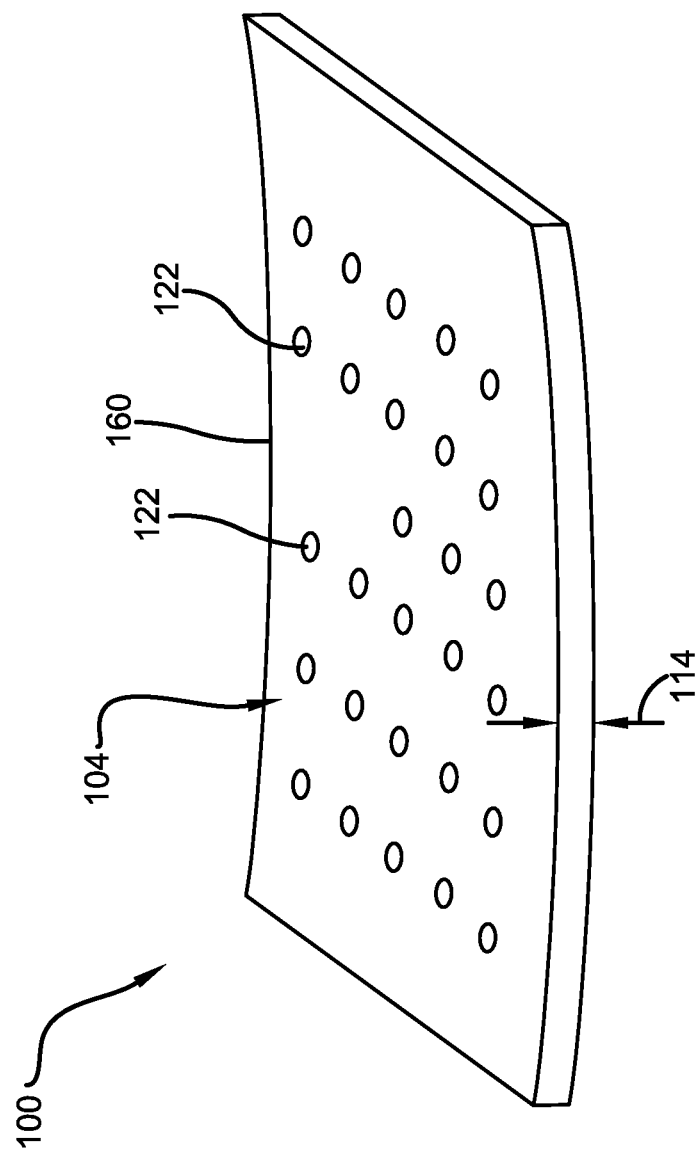
FIG. 2 illustrates a bottom perspective view of one potential embodiment of the oral procedure bacteria spread prevention tool of the present invention in accordance with the disclosed architecture.

FIG. 2 illustrates a rear perspective view of the oral procedure bacteria spread prevention tool of the present invention in accordance with the disclosed structure. As shown in the FIG. 2, the bottom layer 104 is present at the side of the tool 100, which is closer to the patient's mouth. The bottom layer 104 comprises a plurality of small holes 122 which are geometrically-arranged to form a pattern. The holes 122 can be arranged in straight lines or in any other shape. Each of the holes 122 can generally be about 1 mm to about 6 mm in diameter. The dimensions of the small holes 122 and the connector hole 110 are not so limited, and can be designed to satisfy user need and/or preference.

The bottom layer 104 and the top layer 102 are made up of polycarbonate materials and are transparent in appearance. The transparent bottom layer 104 and top layer 102 allow dental care professionals to easily view the oral cavity of the patients from a distance, and perform dental procedures while being protected against the transmission of germs and diseases. The spread prevention tool, in another potential embodiment, includes magnifying bottom and top layers to enhance viewing of the oral area of a patient therebelow (not illustrated).

Figure 3:
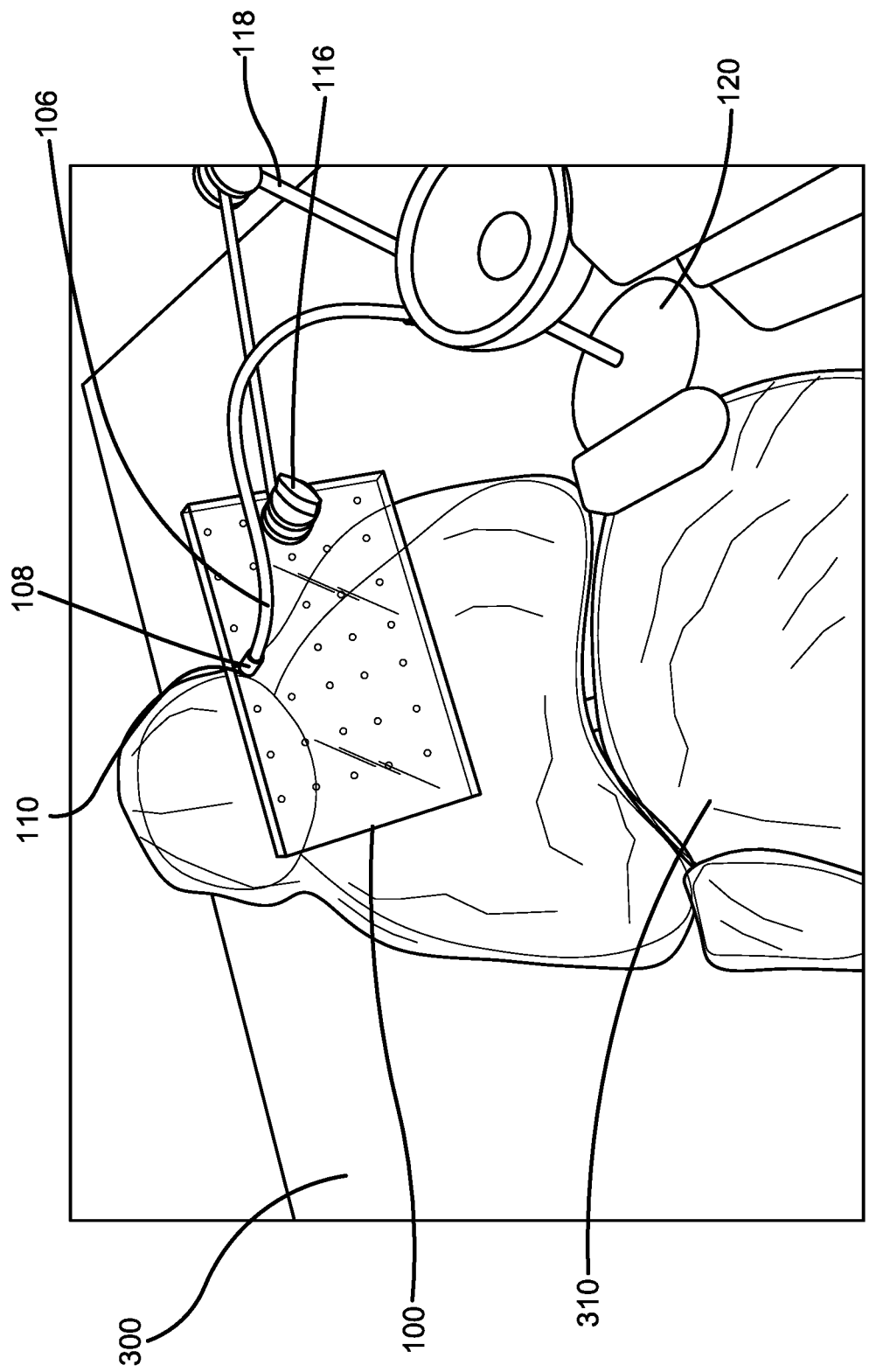
FIG. 3 illustrates a top perspective view of the setup of one potential embodiment of the oral procedure bacteria spread prevention tool of the present invention in a dental healthcare center in accordance with the disclosed architecture.

FIG. 3 illustrates a perspective view of the set-up of the oral procedure bacteria prevention tool of the present invention in a dental healthcare center in accordance with the disclosed architecture. As shown, the oral procedure bacteria spread prevention tool 100 is setup in a dental healthcare center 300. The oral procedure bacteria spread prevention tool 100 is securely held using the stand connector 116, which enables the dental care professionals to set the reach and height of the tool via the stand 118, and make adjustments as per the requirements for the oral health check-ups and treatment procedures. Typically, the stand 118 is adjusted at a reach and a height such that the tool 100 is placed at a distance of 4 to 6 inches from the oral cavity of the patient sitting on a dental chair 310.

Additionally, the polycarbonate layer structure is held by the stand connector 116 in a manner such that the connector hole 110 is centrally-positioned above the oral cavity of the patient while the patient is seated on the dental chair 310 for any oral health check-ups or dental procedures. The stand connector 116 can be a knob-like structure, which can be relaxed to increase a gap in between the knob structure to hold the polycarbonate layer structure, and the knob can be tightened to decrease the gap of the knob structure, to improve the grip for holding the polycarbonate layer structure of the bacteria spread prevention tool 100.

Figure 4:
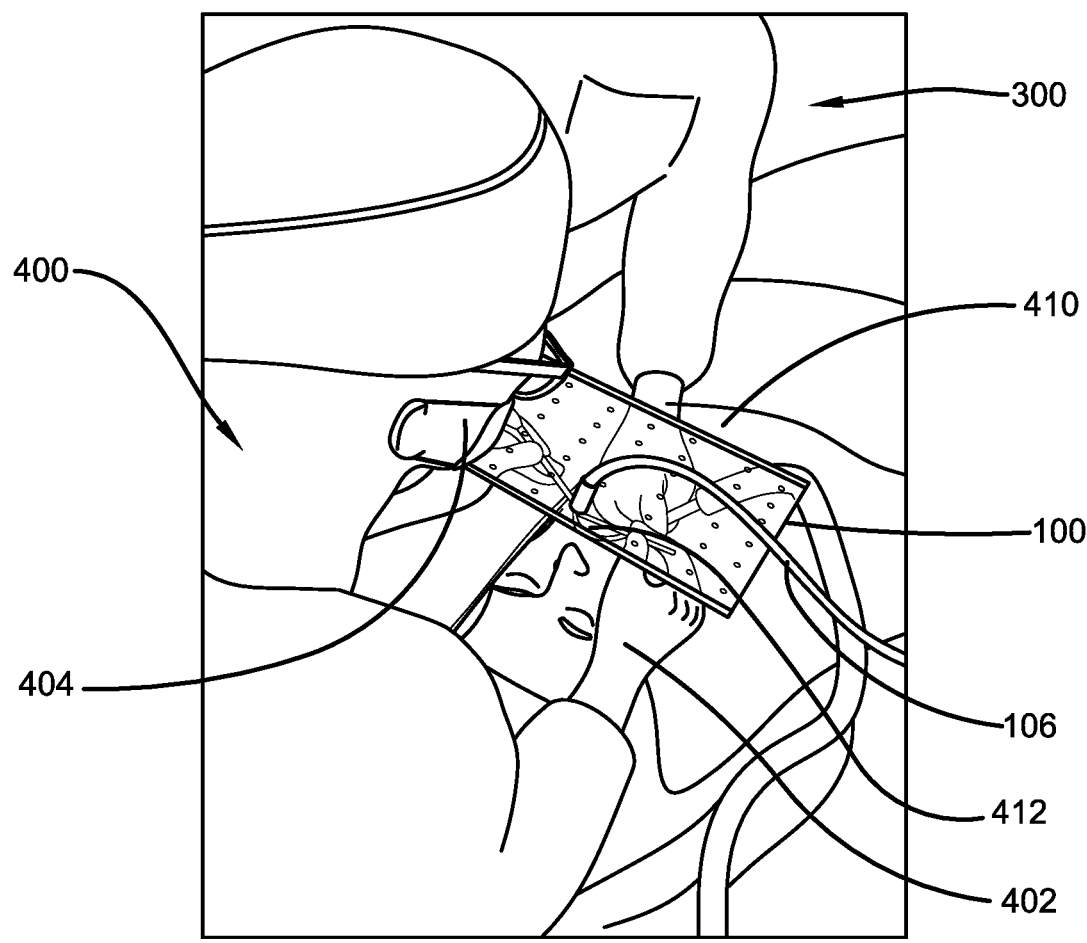
FIG. 4 illustrates a top perspective view of a dentist using one potential embodiment of the oral procedure bacteria spread prevention tool of the present invention in a dental healthcare center in accordance with the disclosed architecture.

FIG. 4 illustrates a perspective view of a dentist using the oral procedure bacteria spread prevention tool of the present invention in a dental healthcare center in accordance with the disclosed structure. As shown, the bacteria spread prevention tool 100 is set up in a dental healthcare center 300. A patient 410 is seated on the dental chair for an oral health check-up or dental treatment procedure, and a dentist 400 stands beside the patient 410 for performing the oral health check-up or dental procedures. The tool 100 is placed at a height of 4 to 6 inches from the patient's mouth or oral cavity 412, and forms a barrier between the patient's mouth 412 and the dentist 400 in order to stop the spread of bacteria, aerosols, pathogens and viruses.

The dentist 400 can easily use his/her hands 402 under the tool 100, to perform the dental check-up or procedure on the user's mouth 412, while the tool 100 creates a barrier between the dentist's face 404 and the patient's mouth 412. The suction pipe 106 can be activated using the suction machine 112 while performing the dental procedures, to enable the suction pipe 106 to suck all the germs, bacteria, viruses or other harmful pathogens from the patient's oral cavity that have traveled to the area between the bottom layer 104 and top layer 102, and to reduce the splatter produced during dental procedures. Once the dental procedure is completed, the suction machine can be deactivated to stop the suction mechanism of the suction pipe 106. Accordingly, the suction mechanism can be activated and/or deactivated as per the requirements of the dentists.

The pathogen spread prevention tool 100 of the present invention is advantageous in times of pandemics such as COVID-19, and in other similar situations to stop the spread of bacteria, viruses, germs and other harmful pathogens.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "oral procedure bacteria spread prevention tool", "bacteria spread prevention tool for oral procedures", "bacteria spread prevention tool", "pathogen spread prevention tool" and "pathogen smear or spread protection apparatus" are interchangeable and refer to the oral procedure bacteria spread prevention tool 100 of the present invention.

Notwithstanding the forgoing, the oral procedure bacteria spread prevention tool 100 of the present invention can be of any suitable size and configuration as is known in the art without affecting the overall concept of the invention, provided that it accomplishes the above-stated objectives. One of ordinary skill in the art will appreciate that the size, configuration and material of the oral procedure bacteria spread prevention tool 100 as shown in the FIGS. are for illustrative purposes only, and that many other sizes and shapes of the oral procedure bacteria spread prevention tool 100 are well within the scope of the present disclosure. Although the dimensions of the oral procedure bacteria spread prevention tool 100 are important design parameters for user convenience, the oral procedure bacteria spread prevention tool 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A bacteria spread prevention tool for oral care procedures adapted to inhibit the spread of viruses and pathogens, said bacteria spread prevention tool comprising: a solid top layer of transparent material; a bottom layer of transparent material including a plurality of holes therethrough; said top layer and said bottom layer connected about a perimeter along opposing longitudinal sides and opposing lateral sides including a gap therebetween; said holes for enabling transmission of some aerosol and pathogens therethrough and for trapping the aerosols and pathogens in said gap between said top layer and said bottom layer; a suction pipe connected to a passage through said top layer for access to said gap; and a suction machine connected to said suction pipe for extracting aerosols and pathogens trapped in said gap from an oral care procedure work area; wherein said top layer and said bottom layer form a convex shape facing downward for deflecting droplets and splatters downward; and further comprising an adjustable stand for connecting to the spread prevention tool to adjust the height and the reach.

2. The bacterial spread prevention tool of claim 1, wherein said gap is between 5 mm and 15 mm between said top layer and said bottom layer.

3. The bacteria spread prevention tool of claim 1, wherein said gap is between 8 mm and 12 mm between said top layer and said bottom layer.

4. The bacteria spread prevention tool of claim 1, wherein said top layer and said bottom layer provide magnification to an oral care procedure work area.

5. The bacteria spread prevention tool of claim 1, wherein said holes include a diameter about 1 mm to about 6 mm.

6. The bacteria spread prevention tool of claim 1, wherein said holes include a diameter about 2 mm to about 5 mm.

7. A bacteria spread prevention tool for oral care procedures adapted to inhibit the spread of viruses and pathogens, said bacteria spread prevention tool comprising: a solid top layer of transparent material; a bottom layer of transparent material including a plurality of holes therethrough; said top layer and said bottom layer connected about a perimeter along opposing longitudinal sides and opposing lateral sides including a gap therebetween; said holes for enabling transmission of some aerosol and pathogens therethrough and for trapping the aerosols and pathogens in said gap between said top layer and said bottom layer; said top layer and said bottom layer form a convex shape facing downward for deflecting droplets and splatters downward; a suction pipe connected to a passage through said top layer for access to said gap; a suction machine connected to said suction pipe for extracting aerosols and pathogens trapped in said gap from an oral care procedure work area; and an adjustable stand for connecting to the spread prevention tool to adjust the height and the reach of the spread prevention tool; wherein said top layer and said bottom layer form a convex shape facing downward for deflecting droplets and splatters downward.

8. The bacteria spread prevention tool of claim 7, wherein said gap is between 5 mm and 15 mm between said top layer and said bottom layer.

9. The bacteria spread prevention tool of claim 7, wherein said gap is between 8 mm and 12 mm between said top layer and said bottom layer.

10. The bacteria spread prevention tool of claim 7, wherein said top layer and said bottom layer provide magnification to an oral care procedure work area.

11. The spread prevention tool of claim 7, wherein said holes include a diameter about 1 mm to about 6 mm.

12. The spread prevention tool of claim 7, wherein said holes include a diameter about 2 mm to about 5 mm.

13. A bacteria spread prevention tool for oral care procedures adapted to inhibit the spread of viruses and pathogens, said bacteria spread prevention tool comprising: a solid top layer of transparent material; a bottom layer of transparent material including a plurality of holes therethrough; wherein said holes include a diameter about 1 mm to about 6 mm; said top layer and said bottom layer connected about a perimeter along opposing longitudinal sides and opposing lateral sides including a gap therebetween; wherein said gap is between 5 mm and 15 mm between said top layer and said bottom layer; said holes for enabling transmission of some aerosol and pathogens therethrough and for trapping the aerosols and pathogens in said gap between said top layer and said bottom layer; a suction pipe connected to a passage through said top layer for access to said gap; a suction machine connected to said suction pipe for extracting aerosols and pathogens trapped in said gap from an oral care procedure work area; and an adjustable stand for connecting to the spread prevention tool to adjust the height and the reach of the spread prevention tool; wherein said top layer and said bottom layer form a convex shape facing downward for deflecting droplets and splatters downward.

14. The bacteria spread prevention tool of claim 13, wherein said gap is between 8 mm and 12 mm between said top layer and said bottom layer.

15. The bacteria spread prevention tool of claim 13, wherein said top layer and said bottom layer provide magnification to an oral care procedure work area.

16. The bacteria spread prevention tool of claim 13, wherein said holes include a diameter about 2 mm to about 5 mm.

* * * * *